United States Patent [19]

Oude Alink et al.

[11] 4,443,609

[45] Apr. 17, 1984

[54] TETRAHYDROTHIAZOLE PHOSPHONIC ACIDS OR ESTERS THEREOF

[75] Inventors: Bernardus A. Oude Alink, St. Louis; Derek Redmore, Webster Groves, both of Mo.

[73] Assignee: Petrolite Corporation, St. Louis, Mo.

[21] Appl. No.: 151,051

[22] Filed: May 19, 1980

[51] Int. Cl.³ .............................................. C07F 9/65
[52] U.S. Cl. .................................... 548/111; 548/146
[58] Field of Search ........................................ 548/111

[56] References Cited

U.S. PATENT DOCUMENTS 4,036,846  7/1977  Barth ............................... 548/111 X

*Primary Examiner*—Richard Raymond
*Attorney, Agent, or Firm*—Sidney B. Ring; Leon Zitver

[57] ABSTRACT

This invention relates to tetrahydrothiazole phosphonic acids or phosphonates and to the preparation thereof by reacting dihydrothiazoles with phosphorous acid or esters thereof.

5 Claims, No Drawings

TETRAHYDROTHIAZOLE PHOSPHONIC ACIDS OR ESTERS THEREOF

In U.S. Pat. No. 4,106,904 there is described the reaction of aldehyde with ammonia. Where the alpha carbon of the aldehyde is unsubstituted, a cyclic compound is formed in accord with the following equation:

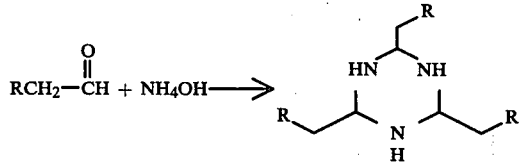

However, as disclosed by Hasek et al J Org Chem 26, 1822 (1961) where the alpha carbon is substituted non-cyclic, compounds are formed in accord with the following reactions:

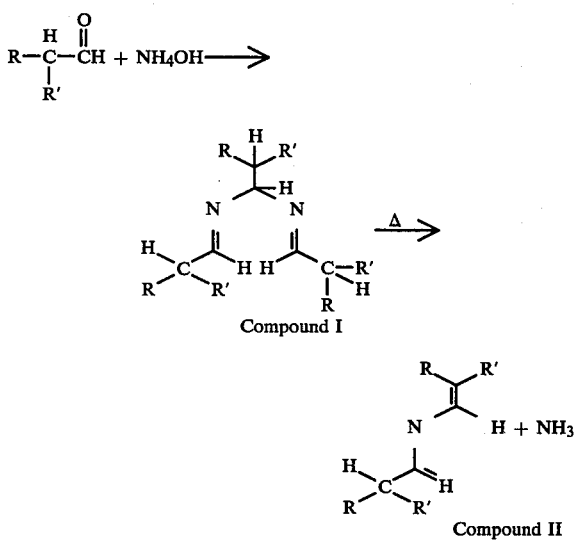

Compound II is the starting material of the present invention. Since Compound I converts substantially quantitatively to Compound II, for purposes of this reaction it is considered an equivalent of Compound II.

Ser. No. 112,506 filed Jan. 16, 1980, now abandoned, further states that when Compounds I and/or II are reacted with sulfur, dihydrothiazoles are formed.

This is illustrated by the following reaction:

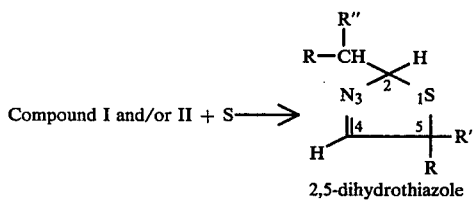

The reaction is carried out by heating a mixture of Compound I or II and elemental sulfur in stoichiometric amounts at temperatures from 40°–160° C. for 1–24 hrs. Solvents which do not interfere with the reaction may be used but are not necessary.

R and R', which are the moieties of the aldehyde reactant, may be any group which does not interfere with the reaction such as alkyl, cycloalkyl, aryl, aralkyl, alkarylalkyl, etc., but preferably alkyl.

Thus, in the dihydrothiazoles of Ser. No. 112,506 of the formula

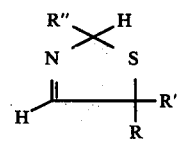

R" is a branched hydrocarbon, preferably branched alkyl such as

where R and R' have the same meaning as the R and R' groups at position 5.

We have now discovered that the 2,5-dihydrothiazoles of Ser. No. 112,506 filed Jan. 16, 1980 can be reacted with phosphorus acid or esters thereof to yield tetrahydrothiazole phosphonic acids or esters thereof.

The reaction may be summarized as follows:

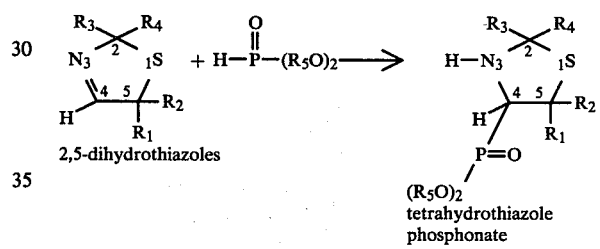

Reaction involves heating the 2,5-dihydrothiazole and an equivalent amount of dialkyl ($R_5$=alkyl) or diaryl ($R_5$=aryl) phosphorous ester or phosphorous acid ($R_5$=H) at temperatures between 30°–180° C. The products derived from reaction of phosphorous acid ($R_5$=H) and the 2,5-dihydrothiazole can also be prepared by hydrolysis of the esters:

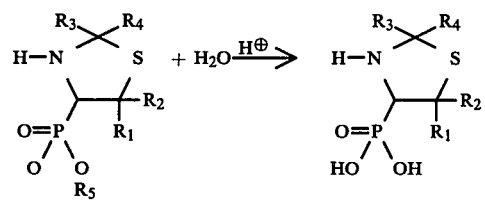

$R_5$ is an alkyl moiety.

Salts of the free acid can also be prepared such as alkali metal salts Na, K, etc., amine salts, ammonium salts, etc. Accordingly, $R_5$ can be an alkyl or aryl moiety, H or a cation.

Reaction times are 1–24 hours. In the dihydrothiazole $R_1$, $R_2$, $R_3$ and $R_4$ may be H, alkyl, cycloalkyl, aryl, aralkyl, etc.

The tetrahydrothiazole phosphonic acids and esters thereof are useful as scale inhibitors (or intermediates leading to scale inhibitors by further reaction with formaldehyde/phosphorous acid), as acid corrosion inhibitors, general corrosion inhibitors, or biocides.

EXAMPLE 1

3,7-Diethyl-5-azanona-3,5-diene

To a sample of 250 grams of 28% ammonium hydroxide was added 215 grams of 2-ethylbutyraldehyde and the heterogeneous mixture was stirred for 18 hours at ambient temperature. The resulting organic layer was separated, and after drying, slowly distilled at atmospheric pressure to yield 148.8 grams of 3,7-diethyl-5-azanona-3,5-diene.

Mass spectrum m/e=181. $^{13}$C nuclear magnetic resonance spectrum, solvent CDCl$_3$, ref. TMS.

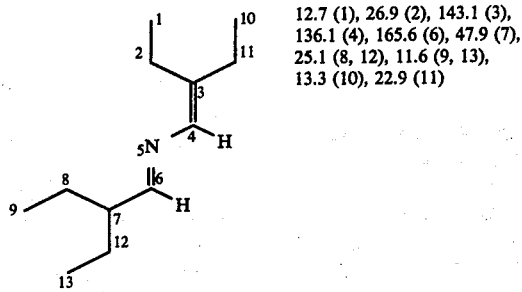

12.7 (1), 26.9 (2), 143.1 (3), 136.1 (4), 165.6 (6), 47.9 (7), 25.1 (8, 12), 11.6 (9, 13), 13.3 (10), 22.9 (11)

EXAMPLE 2

2,5-Dihydro-5,5-diethyl-2-(1-ethylpropyl) thiazole

A sample of 147.8 grams of 3,7-diethyl-5-azanon-3,5-diene, prepared as described in Example 1 and 26 grams of elemental sulfur were heated at 150° C. for 19 hours. The resulting product was distilled under diminished pressure and the fraction b$_{25}$ 145°–150° C., was identified as 128 grams of 2,5-dihydro-5,5-diethyl-2-(1-ethylpropyl)thiazole.

Mass spectrum m/e=213, $^{13}$C nuclear magnetic resonance spectrum, solvent CDCl$_3$, ref TMS.

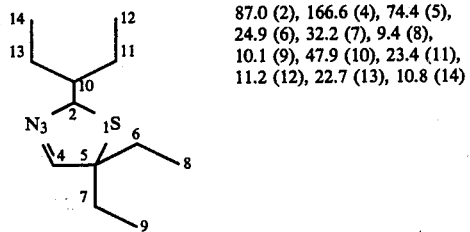

87.0 (2), 166.6 (4), 74.4 (5), 24.9 (6), 32.2 (7), 9.4 (8), 10.1 (9), 47.9 (10), 23.4 (11), 11.2 (12), 22.7 (13), 10.8 (14)

EXAMPLE 3

2,6-Dimethyl-4-azahepta-2,4-diene

To 1400 grams of a 28% solution of ammonium hydroxide was added with stirring over a 4 hours period 1400 grams of isobutyraldehyde while a reaction temperature of 22°–47° C. was maintained. After completion of the addition, stirring was continued for 18 more hours. The resulting organic layer was refluxed under azeotropical conditions until ammonia evolution ceased (14 hours). The resulting 1137.8 grams of product was identified as 2,6-dimethyl-4-azahepta-2,4-diene.

Mass spectrum m/e=125. $^{13}$C nuclear magnetic resonance spectrum, solvent CDCl$_3$, reference TMS.

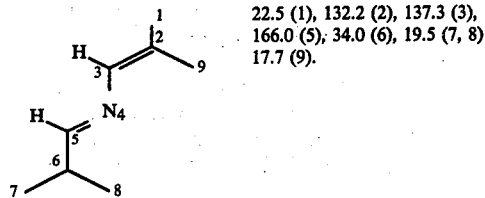

22.5 (1), 132.2 (2), 137.3 (3), 166.0 (5), 34.0 (6), 19.5 (7, 8) 17.7 (9).

EXAMPLE 4

2,5-Dihydro-5,5-dimethyl-2-(1-methylethyl)thiazole

A mixture of 364.9 grams of 2,6-dimethyl-4-azahepta-2,4-diene prepared as described in Example 3 and 93.6 grams of elemental sulfur was heated for 6 hours at 145° C. The resulting product was distilled under diminished pressure and the fraction b$_{25}$ 91°–93° C. was identified as 280 grams of 2,5-dihydro-5,5-dimethyl-2-(1-methylethyl)thiazole.

chemical ionization mass spectroscopy m/e=157, 142, 124, 114, 90, 86.

$^{13}$C nuclear magnetic resonance spectrum, solvent CDCl$_3$, reference TMS.

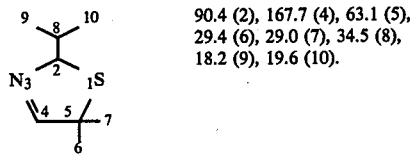

90.4 (2), 167.7 (4), 63.1 (5), 29.4 (6), 29.0 (7), 34.5 (8), 18.2 (9), 19.6 (10).

EXAMPLE 5

Diethyl (2-isopropyl-5,5-dimethyl tetrahydrothiazole) 4-phosphonate

A mixture of 29.5 grams of 2,5-dihydro 5,5-dimethyl-2-(1-methylethyl) thiazole prepared as described in Example 4 and 26 grams of diethylphosphonate was heated for 24 hours at 80° C. The product was cooled to ambient temperature and allowed to crystallize. The resulting product stated in the above title of this example is a mixture of two isomers. The trans isomer (40%) was identified by its $^{13}$C nmr spectrum, solvent CDCl$_3$, reference TMS δ in ppm.

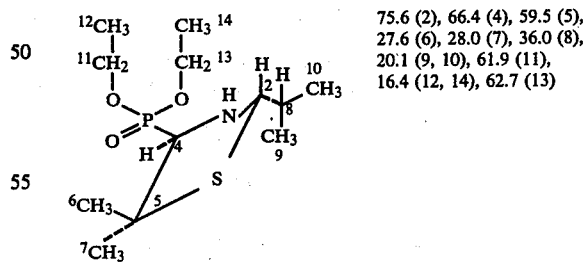

75.6 (2), 66.4 (4), 59.5 (5), 27.6 (6), 28.0 (7), 36.0 (8), 20.1 (9, 10), 61.9 (11), 16.4 (12, 14), 62.7 (13)

The cis isomer (60%) was purified by recrystallization from pentane, large white crystals, mp 72°–73° C.; Infrared spectrum (KBr pellet); 3.07 (N—H), 7.15 and 7.28 [C(CH$_3$)$_2$], 8.00 (P=O), 8.53 (POC$_2$H$_5$), 9.71μ (POC); 'H nmr spectrum, solvent CDCl$_3$, reference TMS, δ in ppm; 4.45 d and 4.12 m (5H), 2.96 d (1H), 2.53 s (1H), 1.87 m, 1.65 s, 1.45 s, 1.34 t, 1.07 d, and 0.96 d (19H), $^{13}$C nmr spectrum, solvent CDCl$_3$, reference TMS, δ in ppm.

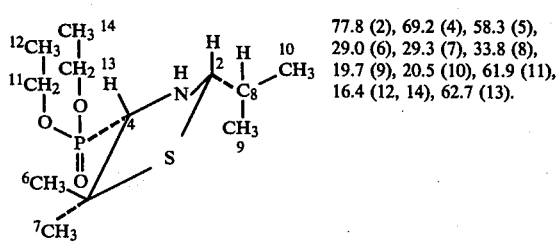

77.8 (2), 69.2 (4), 58.3 (5), 29.0 (6), 29.3 (7), 33.8 (8), 19.7 (9), 20.5 (10), 61.9 (11), 16.4 (12, 14), 62.7 (13).

Anal. Calced for $C_{12}H_{26}NO_3PS$: C, 48.79; H, 8.87; N, 4.74; P, 10.48, S, 10.86; Found: C, 49.04; H, 8.95, N, 4.74; P, 10.65; S, 10.78.

EXAMPLE 6

2-(1-Methylethyl)-5,5-dimethyl tetrahydrothiazole 4-phosphonic acid (Method A)

A sample of 49 grams of diethyl (2-isopropyl-5,5-dimethyl tetrahydrothiazole) 4-phosphonate prepared as described in Example 5, and 50 grams of concentrated hydrochloric acid were refluxed for 48 hours. The resulting acid aqueous solution was washed with ether and evaporated under diminished pressure to yield 42.2 grams of solid. Two crystallization from ethanol afforded small white fluffy needles of 2-(1-methylethyl) 5,5-dimethyltetrahydrothiazole 4-phosphonic acid, mp 225°–226° C.; 'H nmr, solvent $D_2O$/NaOH, δ in ppm, 4.40 d (1H), 2.78 d (1H), 1.96 m, 1.58 s 1.39 s, 0.97 d, 0.94 d (13H).

$^{13}$C nmr spectrum, solvent $D_2O$/NaOH, reference dioxane, δ in ppm;

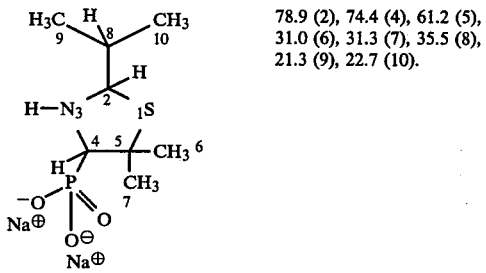

78.9 (2), 74.4 (4), 61.2 (5), 31.0 (6), 31.3 (7), 35.5 (8), 21.3 (9), 22.7 (10).

EXAMPLE 7

2-(1-Methylethyl)-5,5-dimethyl tetrahydrothiazole 4-phosphonic acid (Method B)

A mixture of 31.8 grams of 2,5-dihydro-5,5-dimethyl-2-(1-methylethyl) thiazole prepared as described in Example 4 and 15.0 grams of phosphorous acid were heated slowly to 100° C. An exothermic reaction occurred raising the temperature of the mixture spontaneously to 126° C. After the exothermic reaction subdued, heating was continued to 140° C. and the mixture was kept at this temperature for 4 hours with stirring. The very viscous product solidified upon cooling to ambient temperature and the resulting glass was pulverized and extracted with a mixture of chloroform and water. The chloroform upon evaporation yielded a mixture of 2-isopropyl 5,5-dimethyl-4,5-dihydrothiazole, 2-isopropyl 5,5-dimethyl tetrahydrothiazole and 2,3-diisoproply-5,5-dimethyl tetrahydrothiazole. The aqueous solution was evaporated and afforded 20 grams of a white solid. Repeated crystallization of the solid from ethanol yielded 2-(1-methylethyl)-5,5-dimethyl tetrahydrothiazole 4-phosphonic acid identical in all respects to the product described in Example 6. By methods outlined in Examples 5 and 7 the tetrahydrothiazole phosphonic acid and esters listed in Table I were prepared.

TABLE I

| Example No. | Phosphorus Compound | 2,5-Dihydro thiazole of Ex. | Product |
| --- | --- | --- | --- |
| 8 | Diphenyl-phosphonate | 4 | Diphenyl (2-isopropyl-5,5-dimethyl tetrahydrothiazole) 4-phosphonate |
| 9 | Phosphorus acid | 2 | 2-(1-Ethylpropyl)-5,5-diethyltetrahydrothiazole 4-phosphonic acid |
| 10 | Diethyl-phosphonated | 2 | Diethyl (2-(1-ethylpropyl)-5,5-diethyl-tetrahydrothiazole) 4-phosphonate |

We claim:
1. A tetrahydrothiazole phosphonic acid or phosphonate of the formula

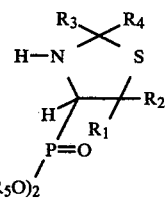

where $R_1$, $R_2$, $R_3$ and $R_4$ are H, alkyl, cycloalkyl, aryl or aralkyl and $R_5$ is alkyl, aryl, H or a cation.

2. A compound of the formula:

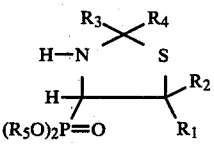

wherein $R_1$, $R_2$, $R_3$, and $R_4$ are hydrogen, alkyl or cycloalkyl and $R_5$ is hydrogen or a cation.

3. The tetrahydrothiazole phosphonate of claim 1 where $R_3$ is a branched alkyl, $R_1$, $R_2$ and $R_5$ are alkyl and $R_4$ is H.

4. A phosphonic acid or phosphonate compound selected from the group consisting of diethyl(2-isopropyl-5,5-dimethyl tetrahydrothiazole)4-phosphonate, 2-(1-methylethyl)-5,5-dimethyl tetrahydrothiazole 4-phosphonic acid, diphenyl(2-isopropyl-5,5-dimethyl tetrahydrothiazole)4-phosphonate, 2-(1-ethylpropyl)-5,5-diethyl tetrahydrothiazole 4-phosphonic acid and diethyl(2-(1-ethylpropyl)-5,5-diethyl-tetrahydrothiazole, 4-phosphonate.

5. The acid or ester compound of claim 4 where said compound is diethyl(2-isopropyl-5,5-dimethyl tetrahydrothiazole)4-phosphonate.

* * * * *